United States Patent
Nekrich (10) Patent No.: US 7,995,815 B2
(45) Date of Patent: Aug. 9, 2011

(54) RADIOLOGY CASE DISTRIBUTION AND SORTING SYSTEMS AND METHODS

(75) Inventor: Robert D. Nekrich, New City, NY (US)

(73) Assignee: Half Moon Imaging, LLC, New City, NY (US)

( * ) Notice: Subject to any disclaimer, the term of this patent is extended or adjusted under 35 U.S.C. 154(b) by 1051 days.

(21) Appl. No.: 11/805,532

(22) Filed: May 23, 2007

(65) Prior Publication Data

US 2008/0292152 A1    Nov. 27, 2008

(51) Int. Cl.
 *G06K 9/00* (2006.01)
(52) U.S. Cl. ....................................................... 382/128
(58) Field of Classification Search .................. 382/128, 382/131, 132; 378/21
See application file for complete search history.

(56) References Cited

U.S. PATENT DOCUMENTS

| | | | | |
|---|---|---|---|---|
| 5,655,084 | A * | 8/1997 | Pinsky et al. | 705/3 |
| 7,532,942 | B2 * | 5/2009 | Reiner | 700/90 |
| 7,657,560 | B1 * | 2/2010 | DiRienzo | 707/999.107 |
| 2002/0080329 | A1 | 6/2002 | Kasahara | |
| 2003/0028084 | A1 | 2/2003 | Kaneko | |
| 2004/0244807 | A1 | 12/2004 | Sun et al. | |
| 2006/0195339 | A1 * | 8/2006 | Backhaus et al. | 705/2 |
| 2006/0260624 | A1 | 11/2006 | Schur et al. | |
| 2007/0136095 | A1 * | 6/2007 | Weinstein | 705/2 |
| 2007/0143136 | A1 * | 6/2007 | Moore et al. | 705/2 |
| 2007/0226008 | A1 * | 9/2007 | Halsted et al. | 705/2 |
| 2007/0255850 | A1 * | 11/2007 | Gould et al. | 709/240 |
| 2008/0144897 | A1 * | 6/2008 | Lal et al. | 382/128 |

OTHER PUBLICATIONS

The International Search Report and the Written Opinion of the International Searching Authority (ISA) dated Oct. 30, 2008.

* cited by examiner

*Primary Examiner* — Matthew C Bella
*Assistant Examiner* — Shervin Nakhjavan
(74) *Attorney, Agent, or Firm* — Edwards Angell Palmer & Dodge LLP; Brian R. Pollack, Esq.

(57) ABSTRACT

The invention provides a system and method for processing an image including means for receiving image information, means for queuing the image information, and means for receiving profile information for a plurality of image analysts. The system can further include means for selecting an image analyst from the plurality of image analysts by comparing the image information from the profile information. The invention also provides a machine readable program including a first input routine for receiving image information, a second input routine for receiving profile information for a plurality of image analysts, and a first run routine for queuing the image information. The machine readable program can also include a second run routine for selecting an image analyst from the plurality of image analysts by comparing the image information to the profile information.

15 Claims, 3 Drawing Sheets

RADIOLOGY CASE DISTRIBUTION AND SORTING SYSTEMS AND METHODS

BACKGROUND OF THE INVENTION

1. Field of the Invention

The present invention relates to a system for distributing images to appropriate image analysts. Particularly, the present invention is directed to a queuing system for processing images.

2. Description of Related Art

A variety of image sorting and distribution systems are known in the art for medical Diagnostic Imaging. Of such systems, many are directed to tele-radiology.

The multi-modality medical field of Diagnostic Imaging has a history dating back to the late $19^{th}$ Century when Wilhelm Conrad Roentgen discovered an unknown energy he termed "X-rays." Advances in medicine and technology over the past 100 years have resulted in a wide variety of imaging modalities such as radiography, fluoroscopy, mammography, computerized tomography ("CT"), ultrasound ("US"), magnetic resonance imaging ("MR"), nuclear medicine ("NM"), bone densitometry, and interventional & angiographic procedures. In the past, images were printed and stored in large file rooms. Today, images may be stored digitally in a Personal Archiving and Communication System ("PACS") and viewed on a computer monitor, printed, or may be digitally transmitted electronically for image analysis and interpretation. The presently accepted data format is called Digital Imaging and Communication in Medicine ("DICOM"). The field of diagnostic image transmission, coined "tele-radiology," initially referred to image transmission across standard telephone lines. With recent advances in high-speed data transmission technology, these images can be transmitted, for example, via Wide Area Networks ("WANs"), Local Area Networks ("LANs"), or Virtual Private Networks ("VPNs") in fractions of seconds.

There has been an exponential surge in medical diagnostic imaging information over recent years—a trend that is likely to continue to accelerate. As of July 2005, the population of the United States was an estimated 295 million, with approximately 78 million "baby-boomers." As the population increases both in quantity and age, so does the number of medical visits and hence diagnostic imaging examination requests. Likewise, as approximately 30% of all healthcare related dollars are spent in the last 3 months of life, the number of diagnostic imaging examinations is accelerating. According to the American College of Radiology, there were approximately 400 million examinations performed in the United States alone in 2001.

With technological advances, especially in multi-detector CT scanners (acquiring up to 256 channels of information simultaneously as well as 3-dimensional generated sagittal and coronal reformats), and new advances in MRI sequences, the number of images acquired per examination continues to increase. Advances in CT and MR angiography have largely replaced the invasive conventional catheter based angiography, and also generate a large number of images. These pose problems for data storage, data transmission, imaging analysis and image interpretation. The number of radiologists in the United States has not been increasing at the same rate of population growth and therefore there is a relative shortage of radiologists. Hence, a referring physician's request for a timely interpretation for the diagnostic imaging study of their patient is sacrificed because of decreased throughput. The term "wet-read" originally referred to a radiologist's interpretation of a radiographic film that was still wet from the film processor and had not had a chance to dry. Today, the term "wet-read" refers to a referring physician's request for any rapid interpretation. While most Emergency Room and Urgent Care Facility generated examinations are appropriately ordered as wet-reads, an increasing number of non-emergent/non-urgent cases have been labeled "wet-read" because of referring physician impatience due to backlogged cases and decreased radiologist throughput. The problem then becomes one of prioritizing the cases properly.

Radiologists in the United States are physicians who have performed radiology residency, some with additional fellowship training allowing for sub-specialization. The American Board of Radiology ("ABR") has rigorous certification procedures that qualify radiologists to interpret these examinations. After completing and passing a series of written examinations, a radiologist becomes "board eligible." Then, a scrupulous oral examination determines "board certification." Continuing medical education requirements ensure the radiologist maintains knowledge on par with advances in technology. As mentioned above, there is a relative shortage of radiologists in the United States. Some proposed solutions include utilizing non-board certified radiologists or by outsourcing the images to non-US based radiologists for analysis. However, radiologists outside the United States are not held to the same high rigorous standards of the ABR and therefore quality may be sacrificed. Additionally, the Medicare Physician Fee Schedule excludes from payment those services that are performed outside of the United States (such as radiographic interpretation).

Most facilities in the United States are not on a completely digital PACS based format, although this is quickly becoming the trend. Large file rooms are being replaced by high capacity computer hard drives which occupy less space and are able to be referenced rapidly without ancillary staffing. In the facilities that do employ a PACS system or are networked for tele-radiology, typically a few radiologists may be responsible for analyzing all cases performed regardless of their sub-specialization. Thus, the most appropriate radiologist may not be interpreting the examination. There is the potential for the sacrifice of quality, and possible erroneous interpretation. Further imaging evaluation may be recommended when unnecessary, may be omitted from recommendation when it should be appropriate, or may be misdirected to an incorrect next best appropriate examination. Improper patient care and subsequent lawsuits may result, with subsequent depositions and court time further removing the radiologist from the act of reading those cases that the radiologist is most suited to read.

Such conventional methods and systems generally have been considered satisfactory for their intended purpose. However, these systems have room for improvement. As evident from the related art, there still remains a continued need for a system capable of matching appropriate image analysts with appropriate images. There also remains a need in the art for a system that can prioritize images to be analyzed in proper order by appropriate image analysts, while being simple and inexpensive to make and use. The present invention provides a solution for these problems.

SUMMARY OF THE INVENTION

The purpose and advantages of the present invention will be set forth in and apparent from the description that follows. Additional advantages of the invention will be realized and attained by the methods, systems, and machine readable program particularly pointed out in the written description and claims hereof, as well as from the appended drawings.

To achieve these and other advantages and in accordance with the purpose of the invention, as embodied herein and broadly described, the invention is directed to a system for processing an image including a means for receiving image information. The system also includes a means for queuing the image information. Also provided is a means for receiving profile information for a plurality of image analysts.

In accordance with a further aspect of the invention, the system may include means for selecting an image analyst from the plurality of image analysts, for example, by comparing the image information with the profile information of the plurality of analysts. In a preferred embodiment, the system may further include means for transmitting the image to the selected image analyst. Also, the system may include means for transmitting the analysis of the selected image analyst.

In accordance with another aspect of the invention, the means for receiving image information may receive the image information from an original medical facility. Further, the means for transmitting the analysis may transmit the analysis to a final medical facility.

In accordance with still another aspect of the invention, the means for queuing may sort the image information into an urgent queue and a routine queue. In a preferred embodiment, the means for selecting may select from the routine queue if the urgent queue is empty.

The invention also includes an article containing a machine readable program containing instructions for controlling a system to perform processing of an image. This machine readable program includes a first input routine for receiving image information. The machine readable program also includes a first run routine for queuing the image information. The machine readable program further includes a second input routine for receiving profile information for a plurality of image analysts.

In further accordance with the invention, the machine readable program may further include a second run routine for selecting an image analyst from the plurality of image analysts by comparing the image information with the profile information. In a preferred embodiment, the machine readable program may further include a first output routine for transmitting the image to the selected image analyst. Also, the machine readable program may include a second output routine for transmitting the analysis of the selected image analyst.

In accordance with another aspect of the invention, the first input routine may involve receiving the image information from an original medical facility. Further, the second output routine for transmitting the analysis may involve transmitting the analysis to a final medical facility.

In accordance with still another aspect of the invention, the first run routine may sort the image information into an urgent queue and a routine queue. In a preferred embodiment, the first run routine for selecting may include only selecting from the routine queue if the urgent queue is empty.

The invention also includes a method for processing an image. This method includes receiving image information. The method also includes queuing the image information. The method further includes receiving profile information for a plurality of image analysts.

In further accordance with the invention, the method may further include a step for selecting an image analyst from the plurality of image analysts by comparing the image information with the profile information. In a preferred embodiment, the method may further include a step for transmitting the image to the selected image analyst. Also, the method may include a step for transmitting the analysis of the selected image analyst, such as to the medical facility that originated the image.

In accordance with another aspect of the invention, receiving image information may involve receiving the image information from an original medical facility. Further, the step for transmitting the analysis may involve transmitting the analysis to a final medical facility.

In accordance with still another aspect of the invention, the step for queuing may include sorting the image information into one of an urgent queue and a routine queue. In a preferred embodiment, the step for selecting may include selecting from the routine queue if the urgent queue is empty.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method, system, and machine readable program of the invention. Together with the description, the drawings serve to explain the principles of the invention.

DETAILED DESCRIPTION OF THE PREFERRED EMBODIMENTS

Reference will now be made in detail to the present preferred embodiments of the invention, examples of which are illustrated in the accompanying drawings. The method and corresponding steps of the invention, as well as the machine readable program of the invention, will be described in conjunction with the detailed description of the system.

The devices and methods presented herein may be used for processing images. The present invention is particularly suited for processing medical images, such as X-ray images. In the setting of a facility employing only a single radiologist, no sorting between radiologists is necessary. However, sorting is still necessary so that the radiologist interprets the emergent/urgent examinations first followed by the routine cases preferably with the oldest case chronologically done first.

In the setting of two or more radiologists, additional sorting parameters can be implemented which may include license status, hospital privilege, subspecialty, and radiologist preferences, among others. It is believed that some radiologists have aversions to certain examinations (e.g., some will not do general modalities such as MRI or mammography, while others will not do specific examinations such as obstetrical ultrasound or post-operative brain PET scans). When a radiologist who will not ultimately be giving their interpretation takes the time to look at an examination, it has a domino effect on efficiency. First, it delays this radiologist from viewing cases that he/she will be reading, thus delaying their interpretation. Also, it delays the appropriate radiologist from his/her analysis as, from his/her perspective, this case has the appearance of being interpreted by a colleague. While 15-20 minutes here or there may not seem significant individually, given the 400-500 million cases performed annually nationwide, this can amount to a substantial time delay. In addition, when a less qualified or less familiar radiologist interprets a case, there may be a time delay due to textbook or journal referencing, internet searching, or asking an associate for his/her opinion. Therefore, allowing the most qualified radiologist to analyze and interpret an examination can improve throughput quality and therefore decrease diagnostic imaging turn-around time.

Thus, in accordance with the invention, a system for processing an image is provided. The system includes means for receiving image information, a means for queuing the image information, and means for receiving profile information for a plurality of image analysts.

Figure 1:
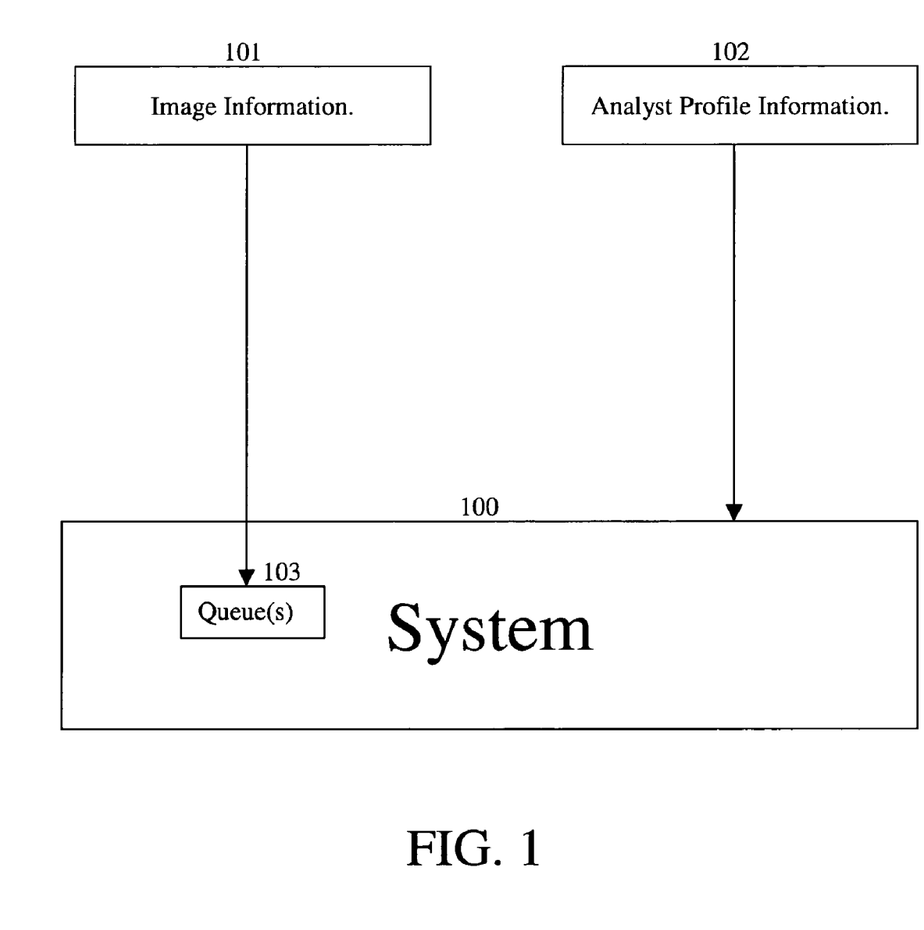
FIG. 1 is a schematic representation of a representative embodiment of a system for processing an image in accordance with the present invention.

For purpose of explanation and illustration, and not limitation, a partial schematic view of an exemplary embodiment of the system in accordance with the invention is shown in FIG. 1 and is designated generally by reference 100. Other embodiments of a system in accordance with the invention, or aspects thereof, are provided in FIG. 2 and FIG. 3, as will be described.

In accordance with the invention, a means for receiving image information is provided having an operable connection with the system.

For purposes of illustration and not limitation, as embodied herein and as depicted in FIG. 1, means for receiving image information 101 is provided with an operable connection to the system. The means for receiving image information 101 can be (by way of example and not limitation) a WAN, a LAN, a VPN, or a web-based system accessed via internet or over wireless/satellite transmission, among others. The image information can include and describe images in one or more of many formats, including preferably Digital Imaging and Communication in Medicine ("DICOM"), or any other image format suitable for transmitting images over a network, including but not limited to JPEG, GIF, and TIF/TIFF file formats, all with or without various degrees of data compression, among others.

The image information may include a variety of types of information including priority, as well as information relating to the content of the image itself. For example, information may be provided relating to the portion of the anatomy being imaged, as well as the type of ailment the patient is suspected of having.

For purposes of illustration only, the image information can include the type of information included in Table I below. Each radiology case has (or potentially could have) the following parameters associated with it.

TABLE I

| | |
|---|---|
| Patient identifier | Patient name |
| | Patient identification/ID number |
| | Date of birth, age |
| | Sex (male, female) |
| Examination specifics | Date of examination |
| | Time of examination |
| | Examination modality (CT, MR, etc) |
| | Body part (brain, chest, etc) |
| | Contrast agents (with, without, or both) and dosage |
| | Pertinent additional information (CT angiography? Multi-phase contrast enhancement? 3-dimensional reformats? Prior examination available for comparision/correlation? Contrast reaction/premedicated? Image timing/delay? etc) |
| | Reimbursement cost (fee per interpretation) |

TABLE I-continued

| | |
|---|---|
| Clinical history | Acute insult/traumatic vs. chronic condition |
| | Pertinent medical history |
| | Pertinent laboratory tests |
| | Post-treatment (history or surgery, radiation, chemotherapy) |
| Facility information | Facility name |
| | Facility location (address, city, state) |
| Referring physician | Referring physician name |
| | Verbal contact info (telephone, beeper number) |
| | Report contact info (fax number, email address) |
| Requested interpretation | Timeliness (emergent/urgent wet-read vs. routine) |
| | Full report vs. preliminary read |
| | Fellowship trained radiologist reading only |
| | Exclude certain radiologists |
| | Specific radiologist requested |

As will be understood, some of the above-referenced parameters (such as examination modality and facility location) may be currently used by some departments of Diagnostic Imaging. If desired, it is possible to use a larger number if not all of the parameters appearing above in Table I alone, or in combination with (but not limited to) those appearing in Table II below. Preferably, these criteria are used to direct the image to a radiologist with a preference for and/or a specialization in diagnosing conditions related to these portions of the anatomy.

TABLE II

| | | |
|---|---|---|
| Radiography | Chest | 1 view, 2 views, decubitus, apical lordotic |
| | Ribs | Unilateral, bilateral |
| | Abdomen | 1 view, 2 views, decubitus, oblique |
| | AC joints | Weight bearing, non-weight bearing, right/left |
| | Shoulder | Internal/external rotation, scapular-Y, axillary, right/left |
| | Clavicle | Right/left |
| | Sternum | |
| | Humerus | Right/left |
| | Elbow | Right/left |
| | Forearm | Right/left |
| | Wrist | Right/left |
| | Hand | Right/left |
| | Finger | Right/left |
| | Pelvis | |
| | Hip | Right/left |
| | Femur | Right/left |
| | Knee | Right/left |
| | Patella | Right/left |
| | Tibia/fibula | Right/left |
| | Ankle | Weight bearing/non-weight bearing, right/left |
| | Foot | Weight bearing/non-weight bearing, right/left |
| | Heel | Right/left |
| | Toe | Right/left |
| | Cervical spine | Standard, oblique, flexion/extension, swimmer's view, shoulder pull |
| | Thoracic spine | |
| | Lumbar spine | Standard, oblique, flexion/extension, upright/supine |
| | SI joints | Right/left |
| | Sacrum | |
| | Coccyx | |
| | Skull | |
| | Sinuses | |
| | Facial bones | |
| | Orbits | Standard, foreign body pre-MRI |
| | Mandible | |
| | TMJ | |
| | Mastoids | |
| | Soft tissue neck | |

TABLE II-continued

| | | |
|---|---|---|
| Fluoroscopy | Scoliosis | |
| | Scanogram | |
| | Skeletal survey | |
| | Esophagram | |
| | Limited esophagram | Lap band cuff placement confirmation/slippage |
| | Swallowing study | |
| | UGI series | |
| | Oral cholecystogram | |
| | Small bowel series | |
| | Cholangiogram | |
| | Barium enema | Single vs. double contrast |
| | Fistulogram | |
| | IVP | |
| | Hysterosalpingogram | |
| | Arthrography | |
| | VCUG | |
| | | All fluoroscopic studies ideally should be read by the radiologist performing the examination |
| Mammography | Screening | |
| | Diagnostic | Unilateral, bilateral |
| Ultrasound | Abdomen | Abdomen, limited, aorta, endoscopic |
| | Renal | Renal, Doppler |
| | Bladder | |
| | Echocardiography | Transthoracic, transesophageal, 2D, M-mode, Doppler, Color Flow |
| | Female pelvis | Transabdominal, transvaginal |
| | Pregnancy | $1^{st}$ trimester, $2^{nd}/3^{rd}$ trimester, biophysical profile |
| | Sonohysterography | |
| | Breast | Unilateral, bilateral |
| | Thyroid | |
| | Male pelvis | Transabdominal, transrectal |
| | Scrotal | |
| | Vascular | Carotid, extremities arterial/venous, ankle/brachial index |
| | Extremities | Non vascular |
| | Pediatric/neonate | Brain, spine, hip |
| CT | Head | With contrast, without contrast |
| | Maxillo-facial/sinus | With contrast, without contrast |
| | Neck | With contrast, without contrast |
| | IAC/mastoid/temporal | With contrast, without contrast |
| | Orbits | With contrast, without contrast |
| | Dentascan | With contrast, without contrast |
| | Cervical spine | With contrast, without contrast |
| | Thoracic spine | With contrast, without contrast |
| | Lumbar spine | With contrast, without contrast |
| | Chest | With contrast, without contrast, hi-resolution |
| | Abdomen | With contrast, without contrast, multi-phase |
| | Abdomen/pelvis | With contrast, without contrast |
| | CT IVP | Contrast delay time |
| | Pelvis | With contrast, without contrast |
| | Extremities | Upper/lower, right/left |
| | Podiatry | Ankle, hindfoot, midfoot, metatarsal/toes |
| | 3D reconstruction | |
| | CT angiography | Chest, aorta |
| Nuclear Med | Bone scan | Whole body, 3 phase, limited, SPECT |
| | Thyroid scan | Thyroid only, whole body, (I-123 or I-131) |
| | Cardiac scan | MUGA, SestaMIBI, thallium, PET scan |
| | Brain scan | ECD, PET scan, brain death, cisternography, SPECT |
| | Gastrointestinal study | Esophageal motility, Gastric reflux/emptying, GI bleeding |
| | Pulmonary | Ventilation/Perfusion (VQ scan) |
| | Infection/inflammation | Gallium, tagged-WBC, FDG-PET |
| | Oncology | |
| | Hepatobiliary scan | Cholescintigraphy (with/without CCK), sulfur colloid |
| | Renal scan | DTPA, MAG3, DMSA, glucoheptonate Renal transplant functionality |
| | Scrotal scintigraphy | |
| | Prostate scintigraphy | SPECT |
| | Endocrine | Adrenal, parathyroid scintigraphy |
| MRI | Head | With contrast, without contrast, angio |
| | Neck | With contrast, without contrast |
| | Face, orbit | With contrast, without contrast |
| | IAC | With contrast, without contrast |
| | Posterior fossa | With contrast, without contrast |
| | Pituitary | With contrast, without contrast |
| | TMJ | With contrast, without contrast |
| | Brachial plexus | With contrast, without contrast |
| | Chest | With contrast, without contrast |
| | Abdomen | With contrast, without contrast |
| | Extremity | With contrast, without contrast; left/right |
| | Shoulder | With contrast, without contrast; left/right |
| | Elbow | With contrast, without contrast; left/right |
| | Wrist | With contrast, without contrast; left/right |
| | Hand | With contrast, without contrast; left/right |
| | Pelvis | With contrast, without contrast |
| | Hip | With contrast, without contrast; left/right |
| | Knee | With contrast, without contrast; left/right |
| | Ankle | With contrast, without contrast; left/right |
| | Foot | With contrast, without contrast; left/right |
| | Podiatry | Ankle, hindfoot, midfoot, metatarsal/toes |
| | Cervical spine | With contrast, without contrast |
| | Thoracic spine | With contrast, without contrast |
| | Lumbar spine | With contrast, without contrast |
| | Sacrum | With contrast, without contrast |
| | Sacral plexus | With contrast, without contrast |
| | Breast | Unilateral, bilateral, with contrast, without contrast |
| Miscellaneous | Bone density/DEXA | |

As imaging facilities are generally located in buildings with fixed locations, the information in Tables I and II above can also be important in those special cases of radiologists' restrictive covenants. Thus, if it is known that a particular radiologist is prevented from performing an image analysis due to a restrictive covenant, this can be accounted for in the sorting system. GPS coordinates can be entered into such programs as Google maps to determine distance between sites. Mobile imaging units, such as MRI and PET/CT units mounted on the back of 18 wheeler trucks, for example also exist which do not permanently reside at a fixed location. The system can be adapted and configured to be aware of these constraints as well. Accordingly, if desired, these cases could be considered as originating from where the images were obtained (such as where the truck is parked) or alternatively with an associated fixed location, such as the primary place of business of the organization that owns the truck bearing the mobile equipment, for example.

Databases that are in operable association with the system of the invention can be continually updated with information regarding imaging facilities that are associated with an imaging group. For example, restrictive covenants relating to individual radiologists and/or imaging groups usually have a time limit. As such, the database can be provided with this information to facilitate sorting.

For example, the restrictive covenant may be associated with an imaging group and not directly with a specific imaging facility. If the imaging group loses it's affiliation with an imaging facility, this facility would no longer be off-limits. If this occurred, the sorting system would know that this particular radiologist could once again interpret images obtained from a certain facility. As such, it would be possible to provide the system with a nationwide geographical database of all imaging facilities, as well as those associated with each imaging group or facility.

In further accordance with the invention, a means for queuing the image information is provided.

For purposes of illustration and not limitation, as embodied herein and as depicted in FIG. 1, means for queuing the image information 102 includes a computer readable storage device accessible where image information can be stored in at least one queue 103, accessible by a queuing program.

A variety of queuing programs are possible. One example by way of illustration and not limitation is a queuing program that places image information that has a high priority into an urgent queue, and information that is not high priority into a routine queue. Accordingly, the program can be adapted to only select images from the routine queue if the urgent queue is empty. In accordance with one embodiment, cases in the urgent queue may be ordered in accordance with the time they enter the queue. Routine cases may also be ordered in accordance with the time they enter the queue. However, it will be appreciated that further criteria may be applied to vary the order of cases within the urgent queue:

1. Time of Acquisition: As described above, processing cases in the order in which they are received ensures that the oldest studies are done first. This is helpful, since as more time goes by, there is an increased chance of an impatient referring physician calling the analyst, which tends to slow down the workflow.

2. Radiologist Specifics: It is possible that a given radiologist is the only one logged onto the system with sufficient expertise to read a certain case. By way of further example, the examination can be a follow-up study for which this radiologist saw a previous examination. Accordingly, in such a situation it is preferred that these cases be read first. If the particular analyst needs to log off the system, this case would have to wait until someone else qualified can interpret it, which could take a significant amount of time.

3. Analyst Preferences: It is also possible that a given analyst (e.g., Radiologist) has a preference for evaluating certain types of cases. For example, even though qualified to do multiple types of exams, a radiologist may prefer to do multiple cases of a certain type (e.g., head CT scans for several hours followed by knee MRIs for several hours). Some radiologists may accordingly find that repeating similar cases in such a manner gets oneself into a routine that may speed up workflow throughput.

4. Multiple Options: Instead of automatically assigning a single further case for the analyst to review, if desired, the system may give the radiologist a choice of two or more cases to review that the radiologist is qualified to analyze. Advantageously, this may cause the radiologist to feel that they have a measure of control or choice, which can help maintain interest of the radiologist, thus increasing efficiency.

5. Compensation: It is also possible for cases to be selected on the basis of compensation to the radiologist, such as where the radiologist is paid a predetermined amount per case. For example, in accordance with one embodiment, a radiologist may select cases that pay the largest amount first. The system may be adapted and configured to track how long it takes the radiologist to analyze/read a certain type of case. For example, this would permit a radiologist in a single hour to read ten cases paying fifty dollars each as opposed to three cases paying seventy-five dollars each. This maximization of the radiologist's profit may accordingly increase efficiency and throughput.

6. Grouping of Similar Cases: In certain circumstances, similar cases can be grouped together, such as for the same patient. For example, it would be preferable for a single radiologist to interpret both left and right knee MRIs of a single patent. Similarly, radiographs of a hand, wrist, and forearm of a single arm of a particular patient are preferably grouped together and not divided among multiple analysts. Likewise, MRI and MR-angiography of a particular patient's brain should be read by the same radiologist. Moreover, similar body parts of different patients can likewise be grouped automatically into lots or batches to increase efficiency, similar in concept to Item 3, above.

7. Blending of Criteria: The above mentioned criteria also can be organized into any desired order. For example, Item No. 2 above is preferably given preference over Item No. 5, above. Similarly, some of the above criteria above may be used to the exclusion of others. Moreover, the any of the above criteria may be used in association with other criteria described herein or otherwise.

In accordance with another embodiment of the invention, cases are sent to the analysts on an as-needed as-available basis. As an example, if two radiologists of equal credentials are reading a group of thirty cases, a system made in accordance with the invention would not simply send fifteen cases to each radiologist. For example, the first radiologist may actually interpret cases twice as quickly as the other. In order to optimize turn-around time, the cases may be advanced to each radiologist on an as-available basis. As such, it is possible that the first radiologist will eventually analyze twenty cases and the other ten cases. Moreover, it can also be advantageous to send cases one at a time in case one of the radiologists has an emergency and encounters a delay interpreting a full batch of cases sent to them. Moreover, if a first case in a batch is difficult and time consuming, this will cause a delay in analyzing the other cases in the batch by the particular radiologist. By way of still further example, if a third or fourth radiologist logs onto the system, if served one at a time, cases will continue to be processed efficiently. However, if all of the cases have already been assigned in large batches, the third and fourth radiologists would remain idle.

In further accordance with the invention, the system includes a means for receiving profile information for a plurality of image analysts. For purposes of illustration and not limitation, as embodied herein and as depicted in FIG. 1, a means for receiving profile information for a plurality of image analysts 102 is provided including a computer readable storage device accessible where profile information can be stored, accessible by a sorting program. It will be understood that any of a variety of computer readable storage devices may be used, such as hard disk storage, system memory, optical drives, combinations thereof, and the like.

Systems currently used in the art, such as PACS and teleradiology systems, do not allow for personalization of the imaging interfaces according to the interpreting radiologist. From the perspective of the originator of the data, each radiologist who has logged on to the system is virtually identical. Thus, systems made in accordance with the invention take these radiologist-specific parameters into consideration as described below in Table III:

TABLE III

| | |
|---|---|
| Radiologist demographics | Name |
| | Board certification (board certified, board eligible, neither) |
| | Location at time of interpretation (in US, outside US) |
| Inclusion criteria | States licensed |
| | Hospitals with obtained privileges |
| | Insurance carriers privileges |
| | Malpractice coverage |
| | Fellowship training |
| | Examination requests (radiologist selects from long list as in previous tables) |
| | Provision for subset sorting, fee per interpretation, etc |
| | Fee per case minimum |
| Exclusion criteria | Examination aversions |
| | Restrictive covenant relative to facility location(s) |
| | Restrictive covenant relative to facility time frame |
| Quality assurance | Peer reviewed evaluations |
| | Real-time data of case turn-around time for specific examinations |
| | Case log |

Such statistical information can also include (but is not limited to) area of specialty, availability, license status, hospital privilege, area of subspecialty, and preferences of the image analyst. Moreover, average turn-around time for a given modality may additionally be used. For example, if a radiologist is especially slow with a certain type of case, they may be advised to not include this type in their acceptable case profile, particularly since a more adept analyst would be likely to interpret the data much more quickly.

In addition to the cases that the radiologist is eligible to interpret, the system is configured so that the radiologist still has access to the demographics of the remaining cases so that the radiologist may change their profile to broaden or narrow their selectivity. In accordance with one aspect of the invention, the radiologist may also inquire about obtaining licenses in other states or to enroll in additional Continuing Medical Education credits to widen their area of expertise.

In further accordance with the invention, the system can further include means for selecting an image analyst by comparing the image information with the profile information. For purposes of illustration and not limitation, this can include a computer routine that is adapted and configured to correlate the image data with that of the analyst to determine the most appropriate analyst to review the image. If desired, this determination can also be founded on docket information on a given analyst. Specifically, a docket, or caseload of the individual analyst can be reviewed by the system. The caseload can include information relating to the backlog of an individual analyst, such as the average amount of time it takes for the analyst to review an image and make a report. A longer average time can indicate that an analyst is overly subscribed. The system can accordingly be configured to direct the image to another analyst that is not as busy. As will be appreciated, any of the criteria described herein may be used to direct appropriate cases to appropriate analysts.

If desired, the system can further include means for transmitting the image to the selected image analyst. The means for transmission can include, for example, a software program that is configured to direct the image information to the image analyst. The image can be transmitted in a variety of manners, such as by way of electronic mail, direct or remote network connection, and facsimile, among others. If desired, the image analyst can be provided with an analyst software program that can access the system from a remote location (such as overseas) as desired. The software program can permit continuous real-time connection of the analyst to the main system and databases, or can be configured for periodic connection, as desired. Thus, in instances where data is being transmitted over low bandwidth connections, periodic connections can be used. For example, if desired, the system can be configured to transmit voluminous data files to the analyst during non-working hours of the analyst, particularly if a low bandwidth connection is used. In this manner, images can be ready for the analyst to review when the analyst arrives at work, even if they took a number of minutes or hours to transmit during non-working hours. However, it will be appreciated by those of skill in the art that such processing of data is merely exemplary, and that image data can be processed at any time and in any suitable manner in accordance with the invention. The image information can be received from an original medical facility where the image information is collected, or from an intermediate facility. For example, the image information can be transmitted from the MRI facility, or from the office of an orthopedist that receives the image information from an MRI facility.

As will be appreciated, the invention can be applied to a system such as a PACS system. In a PACS system, a user typically logs onto the system by way of a terminal. Such a PACS system may be modified to sort and direct cases to appropriate analysts in accordance with the invention. In accordance with this embodiment, a radiologist may be sent a list of patient names including patient information. The particular patient information would be sent in accordance with the teachings herein. By way of further example, the teachings of the invention may be applied to a teleradiology type system in which cases (images and information) are either forwarded to the radiologist's computer (or workstation) or are pulled from the system by the radiologist according to desired criteria, as described herein.

In accordance with a further embodiment, the patient information may originate directly from the imaging facility and be linked to the case. While the information may additionally or alternatively come from the referring physician (e.g., orthopedist), there could be an increased chance for error resulting in a mismatching of information and images. It will be appreciated by those of skill in the art that any suitable individual may be the referring individual, such as but not limited to a physician, technician, office personnel and the like.

The system can further be provided with means for transmitting the analysis of the selected image analyst. The means for transmitting the analysis can be similar to the means for transmitting the image to the image analyst as described above, and can be dependent on the bandwidth available at the time of the transmission. Various means can be used, such as transmission software adapted and configured to transmit the information by way of electronic mail, a direct connection or other network connection, among others. The analysis can be transmitted to a final medical facility, such as one where the patient is being advised at or operated on, or an intermediate facility, such as the office of a surgeon or other medical professional, or other locations. By way of further example, the case report can be sent to the facility sending the case or the referring physician referring the patient. In the case of an imaging center owned by an orthopedist, these may be one-and-the-same. Alternate 'non-final' sites may include specialty consults (other MDs) also involved in this patient's care.

It will be recognized that some or all of the features of the system can be automated and carried out using computer software, while others can be carried out manually. Moreover, radiologists can be used anywhere in the world to interpret and diagnose images originating anywhere in the world.

In accordance with one embodiment of the system, even radiologists half a day apart (e.g., in India, China, or else-where) could be used to evaluate images produced in the United States. Thus, images are generated and routed during the normal working day in the United States. During the next working day in India, for example, the images are evaluated, and reports are directed back to the United States. This permits turnaround of images well within 24 hours or less. If the radiologist in India does not have credentials recognized by the ABR, the system can be configured to direct the analyzed image from the uncertified foreign analyst to an ABR board certified radiologist in the United States to "double check" the work of the uncertified radiologist, and to "certify" it if the certified radiologist agrees that the analysis is correct. However, it is highly preferred to use a certified radiologist.

As will be appreciated, any foreign analyst preferably will have fulfilled the same criteria as those required for radiologists in the US (e.g., board certification, hospital credentialing, etc.). As will be appreciated, there may be certain cases in which the referring physician is not concerned about such credentials. On the other hand, such credentials are required under certain circumstances. By way of further example, Medicare may not necessarily require the radiologist be board certified, but they do require the radiologist to be physically located on U.S. soil when rendering services.

As will be appreciated, in accordance with the invention, it is not necessary for an overnight case to be routed to another country. For example, some U.S. based radiologists prefer to work "off-hours", such as overnight. Moreover, radiologists on U.S. soil in later time zones (e.g., Hawaii) naturally operate on a later schedule than, for example, individuals on the eastern coast of the U.S.

As further may be appreciated by those of skill in the art, some facilities may request a preliminary assessment of image information on an overnight basis. Such assessments may be summarized, for example, in a bullet point format. This preliminary assessment may then be followed by a full report in standard paragraph format. Such an approach tends to be less expensive and facilitates obtaining the essence of the examination (i.e., the preliminary report) as soon as possible after the examination (scan) is performed. Accordingly, such facilities may request such a preliminary assessment from a system in accordance with the invention, and use their own radiologists to generate a full report the next day. Generally, insurance companies require a full report for billing purposes. As can be seen, such a use of preliminary assessments may also increase efficiency and throughput for the given facility.

By way of further example, in accordance with a further embodiment, if a certain case cannot be assigned to a radiologist at a given point in time, such as when the case is initially processed by the system, the system flags the case and also checks to determine if a qualified radiologist will be available to read the case in the near future. If not, the system may notify a system administrator or a subset or all radiologists associated with the system in an effort to locate a radiologist to read the examination. Appropriate communication is then directed by the system to let the referring physician know that there may be a delay in receiving a report.

In accordance with still another embodiment of the invention, a virtual marketplace is provided for performing radiology services. In accordance with this embodiment of the invention, a system is provided as described herein for processing and routing images to radiologists. The system is adapted and configured to permit any radiologist (having approval of the administrator of the virtual marketplace) to log on to the system and read images in accordance with criteria as described herein (e.g., such as user preference, expertise and the like) for any amount of time that the radiologist desires. In accordance with a further aspect of this embodiment of the invention, a radiologist can always be available at any given time to allow for urgent cases.

In accordance with another aspect of the invention, a method for processing an image is provided. The method includes steps of receiving image information, queuing the image information, and receiving profile information for a plurality of image analysts.

Figure 2:
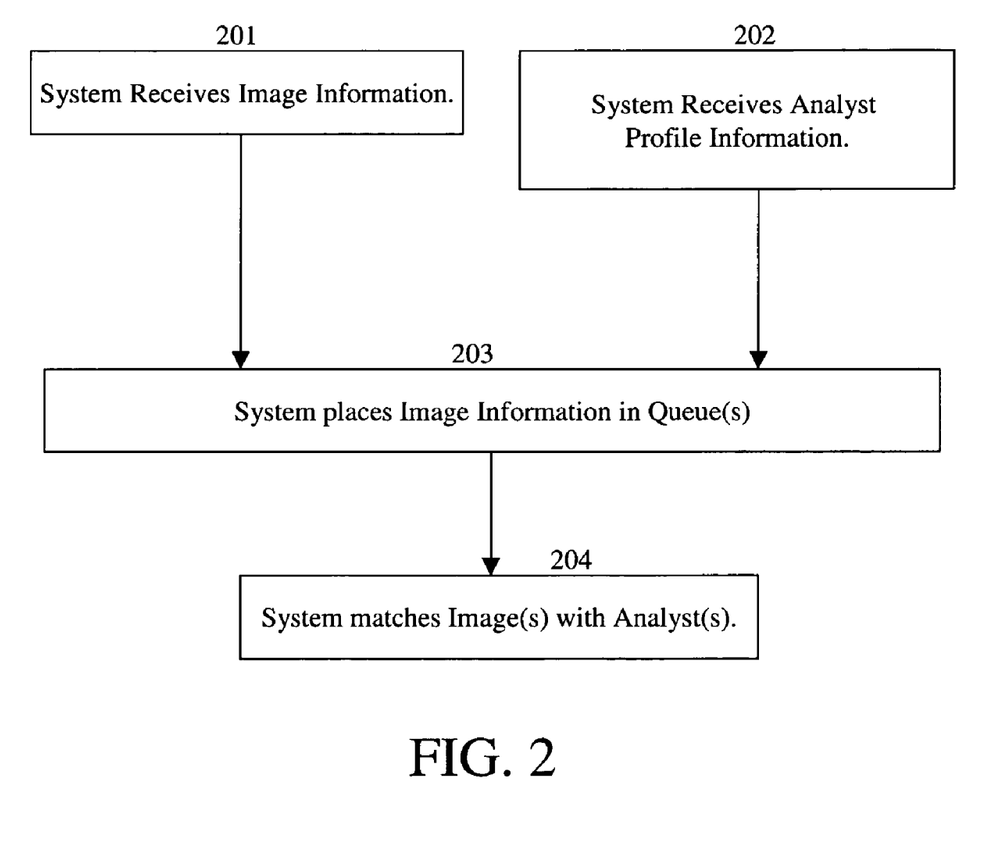
FIG. 2 is a schematic representation of a representative embodiment of a method for processing an image in accordance with the present invention.

For purposes of illustration and not limitation, as embodied herein and as depicted in FIG. 2, the step of receiving image information 201 can include receiving the image information via a network such as a WAN, a LAN, or a VPN, or others, as known in the art. The image information may include or describe images in one or more of many formats, including preferably Digital Imaging and Communication in Medicine ("DICOM"), as well as JPEG, GIF, TIF/TIFF; all with or without various degrees of data compression, among others. The image information can include, for example, the information listed in Tables I and II, above or any other suitable information, including but not limited to that described herein.

In further accordance with the invention, the method includes the step of receiving profile information for a plurality of image analysts. For purposes of illustration and not limitation, as embodied herein and as depicted in FIG. 2, the step of receiving profile information 202 can include receiving statistical information for the image analysts. Such statistical information can include (but is not limited to) area of specialty, availability, license status, hospital privilege, subspecialty, and preferences of the image analysts, as well as the other information described in Table III, above.

In further accordance with the invention, the method includes the further step of queuing image information. For purposes of illustration and not limitation, as embodied herein and as depicted in FIG. 2, the step of queuing image information 203 can include a queuing program that places image information that has a high priority into an urgent queue, and information that is not high priority into a routine queue, among others.

In a preferred embodiment, the method of processing an image can further include a step of selecting an image analyst 204 from a group of image analysts by comparing the image information with the profile information as described herein. In a further preferred embodiment, the step of selecting the image analyst can involve selection from the routine queue only if the urgent queue is already empty.

In accordance with another aspect of the invention, a machine readable program for controlling a system to perform processing of an image is provided. The machine readable program includes a first input routine for receiving image information, a second input routine for receiving profile information for a plurality of image analysts, and a first run routine for queuing the image information.

Figure 3:
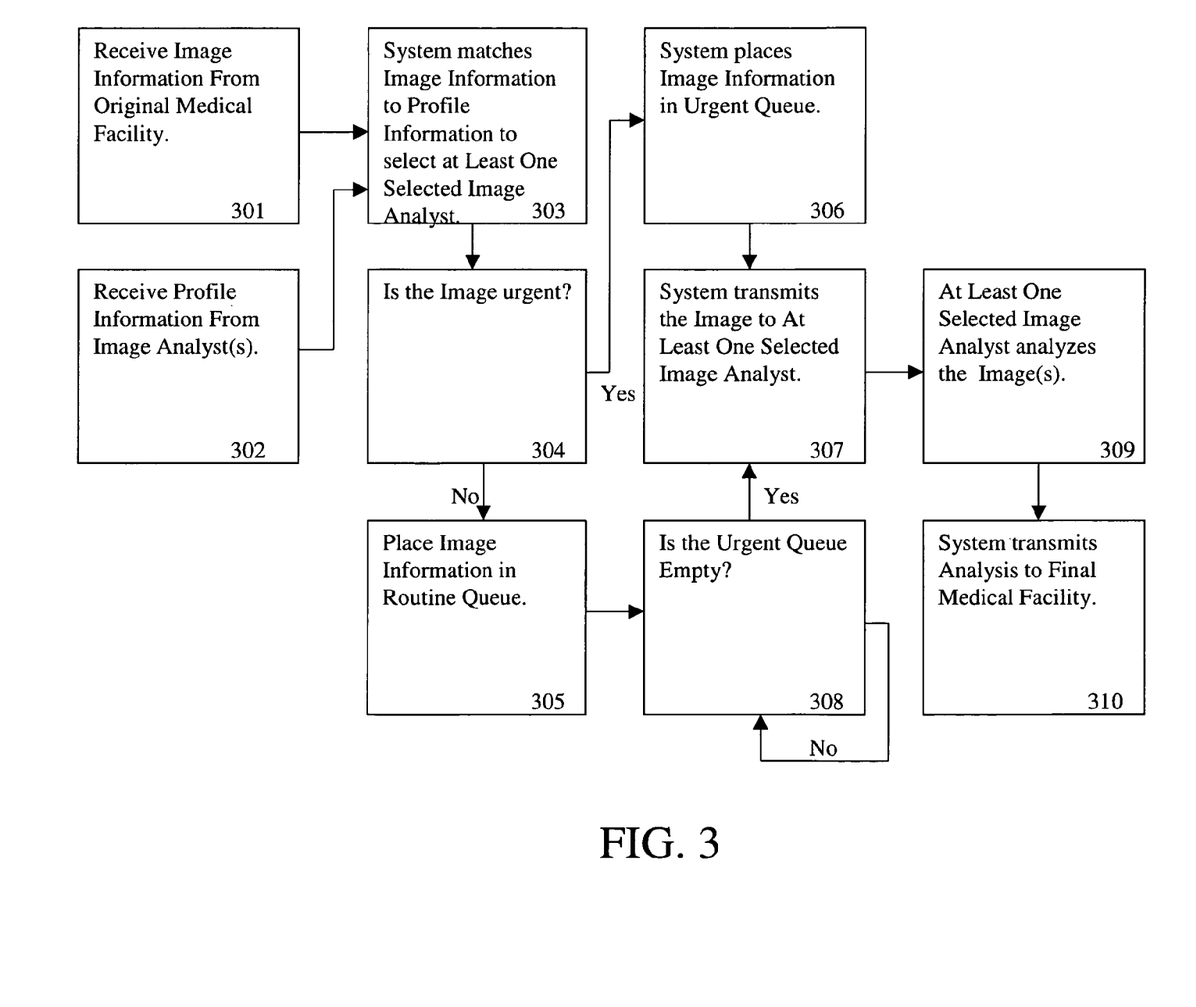
FIG. 3 is a schematic representation of a representative embodiment of a software program for processing an image in accordance with the present invention.

For purposes of illustration and not limitation, as embodied herein and as depicted in FIG. 3, the first input routine 301 can include instructions for receiving image information from an original medical facility, such as a doctor's office, nursing home, specialist office, hospital, hospice and the like. The second input routine similarly can include instructions 302 for receiving profile information for a plurality of image analysts. The various information can be similar to that described in accordance with the description of the system above.

For purposes of illustration and not limitation, as embodied herein, a first run routine 304 for queuing the image information is provided. In one embodiment, the first run routine 304 can place image information that is urgent into an urgent queue 306, and information that is not urgent into a routine queue 305. The first run routine can keep image information from the routine queue in the routine queue until the urgent queue is empty 308.

In a further preferred embodiment, the machine readable program further includes a second run routine 303 that selects an image analyst from a plurality of image analysts by comparing the image information with the profile information as described herein above. One of ordinary skill in the art will readily recognize that the second run routine can select the image analyst before the first run routine queues the image information, at the same time as the first run routine queues the image information, or even after the first run routine queues the image information. FIG. 3 shows by way of example only the embodiment where the second run routine selects the image analyst before the first run routine queues the image information.

In accordance with a further aspect, as embodied herein, the radiologist may also be permitted to return an opened case into the unread queue (303). For example, if a radiologist does not feel qualified to interpret a case after opening it, the radiologist is preferably permitted to return it to the queue for a different radiologist to examine it. While such behavior of returning cases is generally undesirable because it may reduce throughput, it is desirable to the extent that such behavior enhances accuracy. If an analyst returns a significant preselected suitable quantity to the queue, the system may prompt the analyst to re-assess their user preferences, as the preferences may not accurately reflect their abilities.

Another preferred embodiment in accordance with the invention includes a first output routine for transmitting the image to the selected image analyst 307. The first output routine can transmit the image in one or more of many formats, including preferably Digital Imaging and Communication in Medicine ("DICOM"), or any other image format suitable for transmitting images over a network. The selected image analyst can then analyze the image 309. A further preferred embodiment includes a second output routine for transmitting the analysis of the selected image analyst to a final medical facility 310.

Moreover, if in fact the case is being sent to more than one image analyst, then after one radiologist opens the case, the system may accordingly be adapted and configured to send a second signal to all of the other radiologists notifying them that the case has been opened and is already being analyzed.

The computer readable medium on which the computer readable program is contained is preferably selected from the group consisting of a diskette, a computer chip, a computer disk drive and combinations thereof as well as others known in the art. The machine readable program can be written in conventional languages as are known in the art.

In one embodiment of the invention, the system 100 can operate to receive the image information from an original medical facility and transmit the image analysis to a final medical facility. It will be readily appreciated by one of ordinary skill in the art that the original and final medical facilities may in be one and the same.

Preferably, the machine readable program and system are personalized for each radiologist that logs into the system. Each radiologist may be provided with a unique user page tailored to the individual radiologist. The user interface preferably only displays cases for which the radiologist is qualified, and also selects cases in conformance with the user's criteria, as described herein. The user interface also may permit the radiologist to establish or change their preferences for the types of cases that they will receive, as described herein.

All statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Block diagrams and other representations herein represent conceptual views of illustrative circuitry and software embodying the principles of the invention. Thus the functions of the various elements shown in the Figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. The functions of those various elements may be implemented by, for example, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

In the claims hereof any element expressed as a means for performing a specified function is intended to encompass any way of performing that function including, for example, a) a combination of circuit elements which performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. Applicants thus regard any means which can provide those functionalities as equivalent to those shown herein.

Similarly, it will be appreciated that the system flows described herein represent various processes which may be substantially represented in computer-readable medium and so executed by a computer or processor, whether or not such computer or processor is explicitly shown. Moreover, the various processes can be understood as representing not only processing and/or other functions but, alternatively, as blocks of program code that carry out such processing or functions.

The methods and systems of the present invention, as described above and shown in the drawings, provide for a system for processing images and data with superior properties including the ability to expedite image analysis by properly matching images with image analysts and prioritizing analysis with urgent and routine queues. It will be apparent to those skilled in the art that various modifications and variations can be made in the system, machine readable program, and method of the present invention without departing from the spirit or scope of the invention. Thus, it is intended that the present invention include modifications and variations that are within the scope of the appended claims and their equivalents.

What is claimed is:
1. A system for assigning and prioritizing images to be analyzed by image analysts, the system comprising:
   a computer;
   a database storing image information, and storing profile information for a plurality of image analysts;

means within the computer for receiving and transmitting the image information and the profile information from and to the database over a network;

means within the computer for queuing the image information into at least an urgent queue for information that is high priority and a routine queue for information that is not high priority;

means within the computer for assigning a particular image contained within one of the queues to an individual image analyst by comparing the image information for the particular image with the profile information for the plurality of image analysts; and means within the computer permitting the individual image analyst to view the particular image and transmit an analysis of the image over the network;

wherein the means for assigning a particular image to an image analyst are configured to take into consideration the time of acquisition of the particular image as well as the preferences of each analyst.

2. The system of claim 1, wherein the means for assigning a particular image only selects from the routine queue when the urgent queue is empty.

3. The system of claim 1, wherein the preferences of each analyst considered by the means for assigning the individual image include preferred modality used in obtaining the image, and preference for a body part shown in the image.

4. The system of claim 1, wherein the means for assigning a particular image to an individual image analyst is configured to present at least two images to the individual analyst and to allow the individual image analyst to choose the image to which the analyst will be assigned.

5. The system of claim 1, further comprising means for allowing each individual analyst to change their profile information to either broaden or narrow the types of images the individual analyst will accept.

6. The system of claim 1, wherein the means for assigning a particular image to an image analyst are configured to take into consideration analyst-specific parameters that include demographics data, inclusion criteria, exclusion criteria, and quality-assurance data.

7. The system of claim 6, wherein the demographics data includes Board certification and location at the time of the interpretation of the particular image.

8. The system of claim 6, wherein the inclusion criteria includes the following information for each analyst: states where licensed, hospital privileges, insurance carrier privileges, malpractice coverage, fellowship training, and examination requests from the individual analyst.

9. The system of claim 6, wherein the exclusion criteria includes examination aversions and restrictive covenant information.

10. The system of claim 6, wherein the quality assurance data includes peer-reviewed evaluations and real-time data of case turn-around time for specific examinations.

11. A tangible, machine-readable medium encoded with instructions for controlling a system, comprising instructions for accomplishing the following steps:

storing image information, and storing profile information for a plurality of image analysts in a database;

receiving and transmitting the image and profile information from and to the database over a network;

queuing the image information into at least an urgent queue for information that is high priority and a routine queue for information that is not high priority;

assigning a particular image contained within one of the queues to an individual image analyst by comparing the image information for the particular image with the profile information for the plurality of image analysts; and allowing the individual image analyst to view the particular image and transmit an analysis of the image over the network;

wherein the step of assigning a particular image to an image analyst includes taking into consideration the time of acquisition of the particular image as well as the preferences of each analyst.

12. A method of processing a medical image, the method comprising the steps of:

storing image information, and storing profile information for a plurality of image analysts in a database;

receiving and transmitting the image and profile information from and to the database over a network;

queuing the image information into at least an urgent queue for information that is high priority and a routine queue for information that is not high priority;

assigning a particular image contained within one of the queues to an individual image analyst by comparing the image information for the particular image with the profile information for the plurality of image analysts;

presenting the individual image analyst with a user interface for viewing the particular image and transmitting an analysis of the image over the network; and receiving the analysis from the image analyst over the network;

wherein the step of assigning a particular image to an image analyst includes taking into consideration the time of acquisition of the particular image as well as the preferences of each analyst; and wherein each of the steps of the method is carried out using a computer.

13. The method of claim 12, wherein the steps of assigning the particular image and receiving the analysis are accomplished in less than 24 hours.

14. The method of claim 12, further comprising the step of the determining for each image whether the image analyst who has transmitted the analysis is certified according to a given standard.

15. The method of claim 14, further comprising sending the image to a second image analyst who is certified to double-check the analysis when it is determined that the first image analyst is not certified.

* * * * *